(12) United States Patent
Budaraju et al.

(10) Patent No.: US 10,545,494 B2
(45) Date of Patent: Jan. 28, 2020

(54) DETERMINING PERFORMANCE CHARACTERISTICS OF A FERMENTER BATCH OF A BIOFUEL PRODUCTION PLANT

(75) Inventors: Srinivas Budaraju, Austin, TX (US); James F. Bartee, Stilesville, IN (US)

(73) Assignee: Rockwell Automation Technologies, Inc., Mayfield Heights, OH (US)

(*) Notice: Subject to any disclaimer, the term of this patent is extended or adjusted under 35 U.S.C. 154(b) by 1792 days.

(21) Appl. No.: 12/818,757

(22) Filed: Jun. 18, 2010

(65) Prior Publication Data

US 2011/0312003 A1     Dec. 22, 2011

(51) Int. Cl.
    *C12M 1/36*     (2006.01)
    *G05B 23/02*    (2006.01)
    *C12M 1/00*     (2006.01)

(52) U.S. Cl.
    CPC ......... *G05B 23/0235* (2013.01); *C12M 21/12* (2013.01); *C12M 41/48* (2013.01)

(58) Field of Classification Search
    CPC ............................ C12M 21/12; C12M 41/48
    See application file for complete search history.

(56) References Cited

U.S. PATENT DOCUMENTS 6,635,441 B2 * 10/2003 Downs et al. ................ 506/26
2008/0167852 A1 * 7/2008 Bartee et al. ................ 703/11

OTHER PUBLICATIONS

Borzani. (2006) Batch ethanol fermentation: the correlation between the fermentation efficiency and the biomass initial concentration depends on what is considered as produced ethanol. Brazilian Journal of Microbiology, 37:87-89.*
Karuppiah et al. (2008) Energy Optimization for the Design of Corn-Based Ethanol Plants. American Institute of Chemical Engineers, 54(6):1499-1525.*
Oxford Dictionary, entry for "conversion factor" (accessed from <http://oxforddictionaries.com/definition/american_english/conversion+factor> on Jan. 22, 2013), 1 page.*
Senn et al. "Classical Methods." in: Roehr. The Biotechnology of Ethanol: Classical and Future Applications (New York, Wiley, 2001), pp. 7-86.*
Valero et al. (1990) Biomass Estimation Using On-Line Glucose Monitoring by Flow Injection Analysis. Applied Biochemistry and Biotechnology, 24/25:591-602.*
Cheng et al. (2009) Production of Ethanol by Fed-Batch Fermentation, Pertanika J. Sci. & Technol., 17(2):399-408.*

(Continued)

*Primary Examiner* — Kara D Johnson
(74) *Attorney, Agent, or Firm* — Fletcher Yoder, P.C.

(57) ABSTRACT

A method for determining performance characteristics of a fermenter batch in a biofuel production plant based on stoichiometry of fermentation reactions, comprising determining a cell mass of a sample of the fermenter batch; a glucose equivalent total (GET) based at least on the cell mass of the sample of the fermenter batch, and a starch to glucose conversion factor (SGCF) based at least on the GET; a total amount of glucose based at least on the SGCF, a volume of ethanol based at least on the total amount of glucose and the GET; at least one of a fermenter yield based at least on the volume of ethanol, and a fermenter efficiency based on the fermenter yield or the volume of ethanol; and generating an output based on the fermenter yield and/or the fermenter efficiency.

22 Claims, 3 Drawing Sheets

(56) References Cited

OTHER PUBLICATIONS

Graves et al. (2007) Interaction effects of lactic acid and acetic acid at different temperatures on ethanol production by *Saccharomyces cerevisiae* in corn mash. Appl Microbiol Biotechnol, 73:1190-1196.*

Marine; Article entitled "Mass Balance and the Quest for Yield"; Novozymes North America, Inc.; Novozymes Webinar Series; Jul. 8, 2009; www.bioenergy.novozymes.com; 21 pages.

Soto et al; Article entitled "Estimation of Ethanol Yield in Corn Mash Fermentations Using Mass of Ash as a Marker," 2005 The Institute of Brewing & Distilling; Publication No. G-2005-0718-268; vol. 111, No. 2, 2005; www.scientificsocieties.org/jib/papers/2005/G-2005-0718-268.pdf; pp. 137-143.

* cited by examiner

DETERMINING PERFORMANCE CHARACTERISTICS OF A FERMENTER BATCH OF A BIOFUEL PRODUCTION PLANT

BACKGROUND

The invention relates generally to control systems, and more particularly to process control employing novel techniques for determining batch performance characteristics of a biofuel production plant.

During the course of operating a biofuel production plant, various parameters may be determined to indicate the performance of the plant. For example, an operator may compare the performance of one batch with previous batches using a parameter. Such comparisons may enable the operator to improve the performance of the plant. One such parameter may be the yield of a fermenter batch, which represents the amount of product created from a given amount of raw material. However, existing methods for determining the fermenter yield suffer from various disadvantages. For example, some methods involve offsite measurements, involve infrequent measurements, are impractical for continuous monitoring, are unreliable, and/or fail to provide yields for individual batches.

BRIEF DESCRIPTION

The present invention provides novel techniques for determining batch performance characteristics of a biofuel production plant. In particular, the present techniques are presented in the context of a fermenter of the biofuel production plant. More particularly, in various embodiments, the performance characteristics may include a fermenter yield, a fermenter efficiency, or both. However, it should be borne in mind that the invention may be applied in a wide range of contexts, in a variety of plants, and in any desired industrial, commercial, private, or other setting.

In accordance with one aspect of the present disclosure, a method for determining performance characteristics of a fermenter batch in a biofuel production plant based on stoichiometry of fermentation reactions includes determining a cell mass of a sample of the fermenter batch; determining a glucose equivalent total (GET) based at least on the cell mass of the sample of the fermenter batch, and a starch to glucose conversion factor (SGCF) based at least on the GET; determining a total amount of glucose based at least on the SGCF, and a volume of ethanol based at least on the total amount of glucose and the GET; determining at least one of a fermenter yield based at least on the volume of ethanol, and a fermenter efficiency based on the fermenter yield or the volume of ethanol; and generating an output based on the fermenter yield and/or the fermenter efficiency.

In accordance with another aspect, a computer-readable storage medium includes computer code disposed on the computer-readable storage medium. The code includes instructions for determining the performance characteristics of a fermenter batch in a biofuel production plant based on stoichiometry of the fermentation reactions and results of periodic samples of a fermenter recirculation loop and/or results of a sample of a fermenter drop. The instructions include instructions for determining a cell mass of a sample of the fermenter batch; instructions for determining a GET based at least on the cell mass of the sample of the fermenter batch, and a SGCF based at least on the GET; instructions for determining a total amount of glucose based at least on the SGCF, and a volume of ethanol based at least on the total amount of glucose and the GET; instructions for determining at least one of a fermenter yield based at least on the volume of ethanol, and a fermenter efficiency based on the fermenter yield or the volume of ethanol; and instructions for controlling operating parameters of a fermenter and/or a duration of the fermenter batch based upon the performance characteristic determinations.

In accordance with a further aspect, a process controller for controlling the operating parameters of a fermenter and/or a duration of a fermenter batch in a biofuel production plant includes a computer-readable storage medium comprising computer code disposed on the computer-readable storage medium. The code comprises instructions for determining the operating parameters of the fermenter and/or the duration of the fermenter batch in the biofuel production system. The instructions include instructions for determining a cell mass of a sample of the fermenter batch; instructions for determining a GET based at least on the cell mass of the sample of the fermenter batch, and a SGCF based at least on the GET; instructions for determining a total amount of glucose based at least on the SGCF, and a volume of ethanol based at least on the total amount of glucose and the GET; instructions for determining at least one of a fermenter yield based at least on the volume of ethanol, and a fermenter efficiency based on the fermenter yield or the volume of ethanol; and instructions for controlling the operating parameters of the fermenter and/or the duration of the fermenter batch based upon the performance characteristic determinations.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
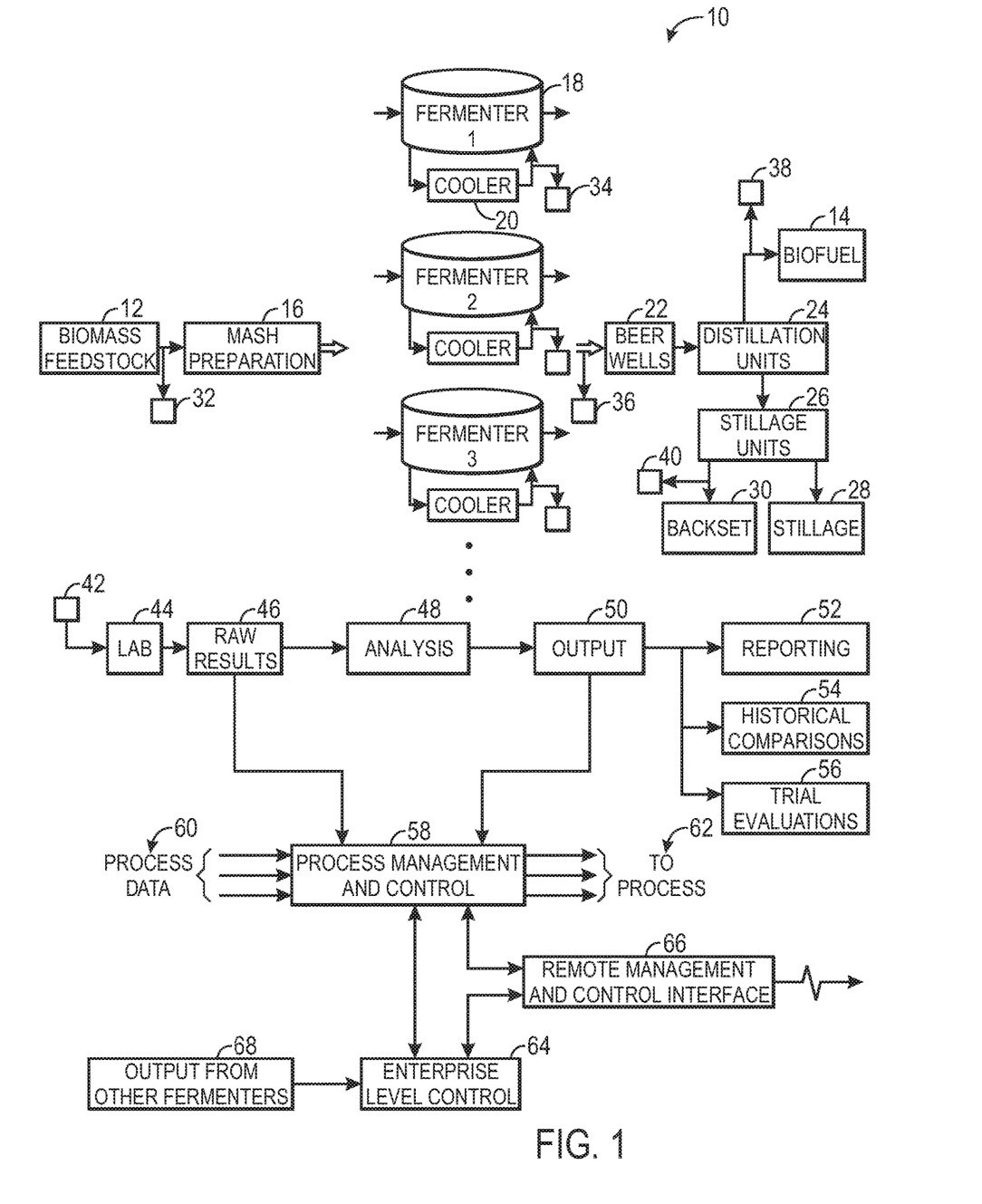
FIG. 1 is a diagram of an exemplary biofuel production plant.

FIG. 1 is a diagram of an exemplary biofuel production plant 10 illustrating how biomass feedstock 12 may be processed through several stages to produce biofuel 14. For example, the biofuel production plant 10 may be a dry mill ethanol facility that produces ethanol from corn by grinding corn kernels into flour and then forming a slurry by adding water, enzymes, yeast, nutrients, and/or other additives. Although the following discussion pertains to dry mill facilities, certain embodiments may also be applicable to wet mill ethanol facilities that produce ethanol by soaking corn in sulfuric acid and water prior to grinding. Returning to FIG. 1, one or more of the various stages in the biofuel production plant 10 may be susceptible to exemplary methods of determining performance characteristics, such as fermenter yield and fermenter efficiency, as described in detail below. In FIG. 1, biomass 12 may first be provided to a mash preparation process 16, where water (which may include recycled water) may be added and the biomass 12 may be broken down to increase the surface area-to-volume ratio. This increase in surface area may allow for sufficient interaction of the water and biomass 12 surface area to achieve a solution of fermentable sugars in water. For example, the starch included in corn may be converted into sugars, such as glucose. The mixture, a biomass 12 and water slurry, may be cooked to promote an increase in the amount of contact between the biomass 12 and water in solution and to increase the separation of carbohydrate biomass from non-carbohydrate biomass. The output of the mash preparation process 16 (i.e., the fermentation feed or mash) may then be sent to a fermentation process, where one or more fermenters 18 may operate to ferment the biomass/water mash produced by the mash preparation process 16.

In the fermenters 18, yeast and enzymes may convert the biomass 12 into a biofuel 14 and by-products, such as carbon dioxide, water, and non-fermentable biomass (solids). For example, the glucose produced in the mash preparation 16 may be converted into ethanol in the presence of yeast and enzymes. Heat generated by fermentation is removed by coolers 20. The fermentation process is a batch process and may include multiple fermenters and coolers operating in parallel (indicated by the vertical ellipsis). The batch start times may be staggered in order to optimize the utilization of the capacity of the beer wells 22 and smoothly distribute the flow of fermentation feed to the fermentation process and the flow of biofuel 14 and stillage as output from the fermentation process.

After being temporarily stored in the beer wells 22, the output from the fermenters 18 may be sent to a distillation process, e.g., one or more distillation units 24, to separate biofuel 14 from water, carbon dioxide, and non-fermentable solids. If the biofuel 14 has to be dehydrated to moisture levels less than 5% by volume, the biofuel 14 may be processed through a processing unit called a molecular sieve or similar processing units. The finalized biofuel 14 may then be processed to be denatured and unfit for human consumption.

The distillation units 24 may separate the biofuel 14 from water. Water may be used in the form of steam for heat and separation, and the condensed water may be recycled back to the mash preparation process 16. Stillage 28 (non-fermentable solids and yeast residue), the heaviest output of the distillation units 24, may be sent to stillage processing units 26 for further development of co-products from the biofuel 14 production process.

The stillage processing units 26 may separate additional water from the cake solids and recycle the water, referred to as backset 30, back to the mash preparation process 16. The backset 30 may include both dissolved and suspended solids. Several stillage processing options may be utilized, including: (1) selling the stillage with minimal processing and (2) further processing the stillage by separating moisture from the solid products via one or more centrifuge units. Using the centrifuge units, the non-fermentable solids may be transported to dryers for further moisture removal. A portion of the stillage liquid (concentrate) may also be recycled back to the fermenters 18. However, the bulk of the flow may generally be sent to evaporator units, where more liquid may be separated from the liquid stream, causing the liquid stream to concentrate into syrup, while solid stillage may be sent to a drying process, e.g., using a drying unit or evaporator, to dry the solid stillage to a specified water content. The syrup may then be sent to a syrup tank. Syrup in inventory may be processed using a number of options. For instance, the syrup may be: (1) sprayed in dryers to achieve a specified color or moisture content, (2) added to the partially dried stillage product, or (3) sold as a separate liquid product. The evaporator units may have a water by-product stream that is recycled back to the mash preparation process 16.

A number of sample points may be provided throughout the biofuel production plant 10 where samples may be drawn for analysis. Results of the analysis of the samples may be used in the exemplary methods of determining batch performance characteristics described in detail below. As these samples are already routinely obtained, the exemplary methods may make use of the existing sample results without increasing laboratory workload. Starting at the beginning of the biofuel production plant 10, a biomass sample point 32 may be used to determine corn and water densities and concentrations of solids and water. Next, fermenter circulation, or recirculation loop, samples 34 may be used to determine concentrations of ethanol, succinic acid, lactic acid, glycerol, acetic acid, and other by-products. After the fermenter batch is complete, a fermenter drop sample 36 may be used to determine the final concentrations of the same components. A biofuel sample 38 may be used to determine ethanol concentration. Finally, a backset sample 40 may be used to determine concentrations of solids and water.

Considering the analysis of a generic sample 42, such as any of the samples described above, the sample 42 may be delivered to a laboratory 44, which may be an on-site laboratory, an in-process analyzer, or an off-site laboratory. A variety of standard laboratory methods may be used for the analysis of the sample 42, including high performance liquid chromatography (HPLC) and pH analysis, which may be commonly available on-site at biofuel production plants 10. The output from these methods will be raw results 46, which may include a chromatogram, a list of percent composition of various components, and/or pH values. The raw results 46 may then be subject to further analysis 48, which may include processing the raw results 46 to determine additional parameters or reformatting the raw results in a more useful configuration. An output 50 that includes the analyzed results may then be used to prepare reports 52 for use by plant operators, engineers, or management, which may be based on the fermenter yield and/or the fermenter efficiency. Further, the output 50 may be used to make historical comparisons 54 to help identify areas of process improvement and/or help schedule future maintenance. Finally, the output 50 may be used to evaluate the effectiveness of trials 56 of various components, such as yeast or corn, or process parameters, such as temperature. Examples of historical comparisons 54 and trial evaluations 56 are provided below.

The raw results 46 and the output 50 may be sent directly to a process management and control module 58. Alternatively, plant operators may input the results manually. With either method of input, the output 50 may be used by the module 58 to perform the exemplary methods of determining batch performance characteristics as described in detail below. Additional inputs to the module 58 may include process data 60, such as temperatures, flow rates, pressures, and/or levels. Operators may be able to monitor the process data 60 and interact with the module 58 to provide new set points, for example. Based on the laboratory results, process data 60, input from operators, programming, and/or other inputs, the module 58 sends output signals 62 to the process.

The output signals 62 may be used to manipulate equipment, such as valves, motors, and pumps. In addition, the module 58 may send process information to an enterprise level control module 64, which may be used to manage all information and functions of a business. The enterprise level control module 64 may also be referred to as an enterprise analyzer. In certain embodiments, the enterprise level control module 64 may receive the output 50 directly instead of through the process management and control module 58. Information may be shared between a remote management and control interface 66 and both the process management and control module 58 and enterprise level control module 64. The interface 66 enables operators, engineers, and/or management at a remote location to monitor and/or interact with both the process management and control module 58 and enterprise level control module 64. Finally, the enterprise level control module 64 may receive output from other disparate fermenters of the same or different biofuel production plants 10. The enterprise level control module 64 may perform comparisons using the output 50 and other output 68 to determine performance outputs associated with such comparisons. Such performance outputs may then be used to adjust the operation of the fermenter 18.

Figure 2:
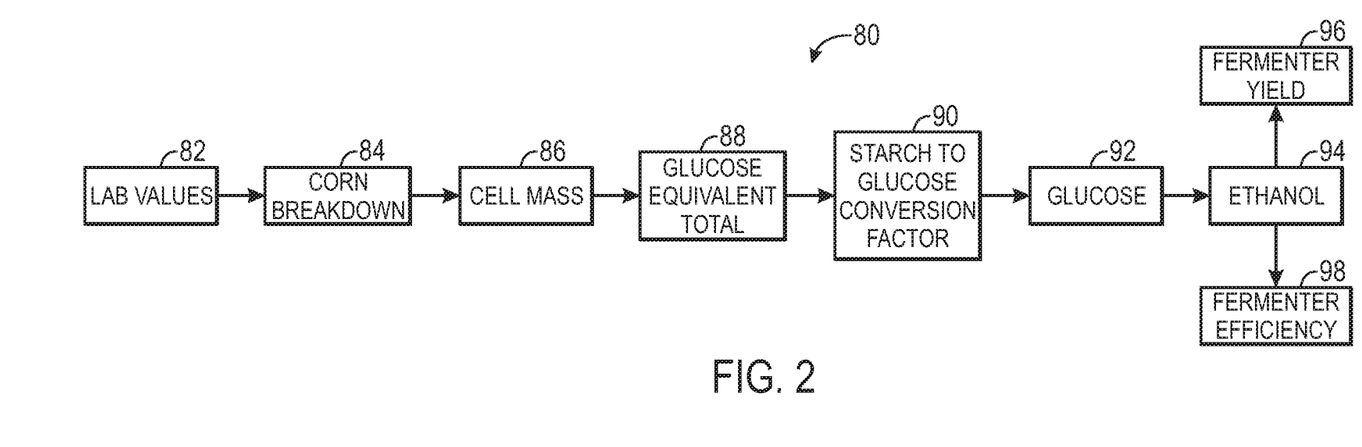
FIG. 2 is a flowchart of an exemplary method for predicting performance characteristics of the biofuel production plant of FIG. 1.

FIG. 2 is a flowchart of an exemplary method 80 for predicting performance characteristics of the biofuel production plant 10 of FIG. 1. An embodiment of the invention may be embodied in the form of computer-implemented processes and apparatuses for practicing those processes. Embodiments of the present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing embodiments of the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via wireless transmission, wherein when the computer program code is loaded into and executed by a computer, the computer becomes an apparatus for practicing embodiments of the invention. When implemented on a general-purpose processor, the computer program code segments configure the processor to create specific logic circuits. A technical effect of the method 80 may include, among others, the determination of performance characteristics of the biofuel production plant 10 based on stoichiometry of the fermentation reactions.

Specifically, the process management and control module 58 may include computer code disposed on a computer-readable storage medium or a process controller that includes such a computer-readable storage medium. The computer code may include instructions for determining the performance characteristics of the fermenter batch of the biofuel production plant 10. In other embodiments, the computer code may include additional instructions. For example, the code may include instructions for inputting the results of the periodic samples of the fermenter recirculation loop 34 and/or results of the sample of the fermenter drop 36. The computer code may also include instructions for controlling operating parameters of the fermenters 18 and/or the duration of the fermenter batch based upon a change in fermenter yield as a function of time. In other embodiments, the code may include instructions for determining an economic cost of energy utilized within the biofuel production plant 10 and determining an economic value of products produced by the biofuel production plant 10. In further embodiments, the instructions for controlling the operating parameters of the fermenters 18 and/or the duration of the fermenter batch may be based on the economic cost and economic value determinations.

Returning to FIG. 2, the method 80 includes obtaining HPLC, or more generally liquid chromatography, sample results that indicate the concentrations of fermentation products, including ethanol. Using these results and the stoichiometry of the fermentation reactions, a total amount of glucose to generate the fermentation products is estimated. Finally, an amount of starch to generate the glucose can be estimated and used to determine the performance characteristics of the batch. The steps of the method 80 are described in detail below. Several conventions are observed in the discussion that follows. The basis of all calculations is 1 bushel of corn (or kilogram, liter, or any other suitable unit of mass or volume). In addition, all masses are in kilograms (kg) unless otherwise stated. Concentrations may be based on sample results or estimated and are expressed in weight percent per unit volume. Finally, any empirically derived values are exemplary and other values may be substituted depending on a particular application.

The first step of the method 80 involves collecting lab values 82 from the sample points discussed above. The sample points may include the biomass sample point 32, the fermenter circulation sample point 34, the fermenter drop sample 36, the biofuel sample point 38, the backset sample point 40, or various other sample points that may exist in the biofuel production plant 10. As mentioned above, because such samples are already being obtained in biofuel production plants 10, the method 80 does not increase the sample load of the laboratory 44, thus distinguishing the method 80 from other methods.

Next, a breakdown 84 of the biomass feedstock 12 is determined. Although corn is referred to as the biomass feedstock 12 in the following discussion, other examples of biomass feedstock 12 include, but are not limited to, sugar cane, plants, wood, yard clippings, garbage, wastes, or combinations thereof. Specifically, the corn breakdown 84 may include the amounts, or masses or weights, of the following components of 1 bushel of corn: starch, glucose, water, solids, and/or other components. The mass of 1 bushel of corn $M_{corn}$ may be determined based on the following equation:

$$M_{corn} = \frac{48.501 + 0.3146 C_{corn\,moisture} + 0.0101 C_{corn\,moisture}^2}{2.202} \quad \text{(Eq. 1)}$$

where $C_{corn\,moisture}$ is the concentration of moisture in the corn (also referred to as corn moisture), the values in the numerator are empirically values derived from a curve fit of published corn data, and the value in the denominator is used for unit conversion. The corn moisture may be measured or estimated and is commonly provided with each delivery of corn to the biofuel production plant 10.

Knowing $M_{corn}$, the mass of starch in the corn $M_{starch}$ may be determined based on the following equation:

$$M_{starch} = \frac{(M_{corn} C_{starch}/100)(1 - C_{corn\,moisture}/100)}{1 - C_{corn\,moisture}} \quad \text{(Eq. 2)}$$

where $C_{starch}$ is the concentration of starch in the corn. Similarly, the mass of glucose in the corn $M_{glucose}$ may be determined based on the following equation:

$$M_{glucose} = \frac{(M_{corn}C_{glucose}/100)(1 - C_{corn\,moisture}/100)}{1 - C_{corn\,moisture}} \quad \text{(Eq. 3)}$$

where $C_{glucose}$ is the concentration of glucose in the corn. The mass of other components in the corn may be determined using equations similar to Eqs. 2 and 3. The mass of water in the corn may be determined by multiplying the mass of corn by the corn moisture. The mass of solids in the corn may be determined by adding together the mass of starch and the mass of other components. The masses determined above for the corn breakdown are used in subsequent calculations described below.

In the next step of FIG. 2, the cell mass 86 is determined. Cell mass refers to mass of yeast per unit volume and may be determined using the following equation:

$$\text{Cell Mass} = \frac{0.056 C_{EtOH}}{0.8202} \quad \text{(Eq. 4)}$$

where $C_{EtOH}$ is the concentration of ethanol in the sample and the numerical values are empirically determined based on the particular strain of yeast used during fermentation. The sample may be obtained from the fermenter circulation sample point 34, the fermenter drop sample 36, the biofuel sample point 38, or from other ethanol-containing locations in the biofuel production plant 10. Next, the GET 88, which represents a theoretical amount of glucose to produce the fermentation products, such as ethanol, is determined using the following equation:

$$GET = C_{dextrose} + C_{succinic\,acid}/1.3191 + C_{lactic\,acid} + C_{glycerol}/1.0224 + C_{acetic\,acid} + C_{EtOH}/0.5114 + \text{Cell Mass} \quad \text{(Eq. 5)}$$

where $C_{dextrose}$, $C_{succinic\,acid}$, $C_{lactic\,acid}$, $C_{glycerol}$, and $C_{acetic\,acid}$ represent the concentrations of dextrose, succinic acid, lactic acid, glycerol, and acetic acid in the sample respectively and the numerical values represent the theoretical yields of the individual products in grams of product per grams of glucose. The concentrations of other products, such as other fermented sugars, may also be included in the determination of the GET. Determination of the theoretical amounts may be based on published stoichiometric coefficients of fermentation reactions.

After determining the cell mass 86 and GET 88, the SGCF 90, which represents the theoretical amount of starch to produced a certain amount of glucose, may be determined using the following equation:

$$SGCF = \frac{(GET(M_{initial\,water} + M_{glucose}/\rho_{glucose} + M_{starch}/\rho_{starch} \times 1.11) - 100 M_{glucose})}{(M_{starch}(109.1 - GET(1.091/\rho_{glucose} - 0.091 - 1/\rho_{starch} \times 1.11)))} \quad \text{(Eq. 6)}$$

where $M_{initial\,water}$ represents the mass of the water in the corn/water mash produced by the mash preparation process 16, which may be determined by adding together the mass of fresh water and the mass of the backset 30. For example, the following equation may be used to determine $M_{initial\,water}$:

$$M_{initial\,water} = \frac{M_{fresh\,water}(1 + (C_{backset}/(100 - C_{backset})))}{\rho_{backset}} \quad \text{(Eq. 7)}$$

where $M_{fresh\,water}$ represents the mass of fresh water added to the mash preparation process 16, $C_{backset}$ represents the concentration of water in the backset 30, and $\rho_{backset}$ represents a density of the backset 30. Returning to Eq. 6, $\rho_{glucose}$ and $\rho_{starch}$ represent densities of glucose and starch respectively. Other numerical values in Eq. 6 are based on the following mass balance equation:

$$1 \text{ kg starch} + 0.091 \text{ kg water} = 1.091 \text{ kg glucose} \quad \text{(Eq. 8)}$$

which shows that water is consumed to convert starch into glucose.

Using the SGCF 90 calculated above, $M_{starch}$, and $M_{glucose}$, the total mass of glucose 92 $M_{glucose\,total}$, which represents both the glucose initially present in the corn and the glucose produced by fermentation of starch in the corn, may be determined using the following equation:

$$M_{glucose\,total} = 1.091 SGCF \times M_{starch} + M_{glucose} \quad \text{(Eq. 9)}$$

where the numerical value is based on Eq. 8. Next, the actual volume of ethanol 94 $V_{EtOH}$ may be determined using the following equation:

$$V_{EtOH} = \frac{(C_{EtOH}/100)/\rho_{EtOH} \times 1000 M_{glucose\,total}}{(GET/100)} \quad \text{(Eq. 10)}$$

where $V_{EtOH}$ is in units of milliliters, $\rho_{EtOH}$ represents the density of the ethanol 94 and the numerical values are used for unit conversion. Knowing the actual volume of ethanol 94 produced by the fermenter 18, the fermenter yield 96 may be determined using the following equation:

$$\text{Yield} = V_{EtOH}/3785 \quad \text{(Eq. 11)}$$

where Yield is in gallons and the numerical value represents a conversion factor from milliliters to gallons. Moreover, the theoretical volume of ethanol that may be obtained from 1 bushel of a standard corn may be defined as approximately 3 gallons of ethanol. Thus, a fermenter efficiency 98 may be determined by dividing the fermenter yield 96 by 3 gallons of ethanol per bushel of standard corn and converting into a percentage using the following equation:

$$\text{Efficiency} = \frac{\text{Yield}}{3} \times 100\% \quad \text{(Eq. 12)}$$

In other words, the fermenter efficiency represents the percentage of a maximum yield based on standard corn. Thus, by defining the yield of standard corn, the efficiency of any particular fermentation batch may be compared against other batches from the same biofuel production plant 10 or batches from different biofuel production plants 10. As discussed above, the fermenter efficiency and/or fermenter yield may be used to generate the output 50 from the fermenter 18 of a biofuel production plant 10, which may then be compared with the output from other disparate fermenters 68 of the same plant or different plants. Such comparisons may be performed by manufacturing execution systems (MES), enterprise resource planning (ERP) systems, enterprise level controllers 64, or enterprise analyzers, for example, and used to improve the operation of many fermenters across an entire business or corporation.

Alternatively, the fermenter efficiency 98 may be determined using other methods, such as by using the following equation:

$$\text{Efficiency} = \frac{C_{EtOH}}{(C_{EtOH} + C_{Total\ Sugars})} \times 100\% \quad \text{(Eq. 13)}$$

where $C_{Total\ Sugars}$ represents the sum of the concentrations of the fermentable sugars. The fermenter efficiency 98 may also be determined using the following equation:

$$\text{Efficiency} = \frac{C_{EtOH}}{C_{Theoretical}} \times 100\% \quad \text{(Eq. 14)}$$

where $C_{Theoretical}$ represents the highest concentration of ethanol that could be obtained given the particular feedstock conditions. Other similar equations may be used to determine fermenter efficiency 98 depending on the available data of a particular application.

The exemplary method 80 described above provides a number of advantages over other alternatives. First, the method 80 uses HPLC sample results and other data that are already readily available to the operators of the biofuel production plant 10, which may enable determination of performance characteristics of individual fermenter batches rather than a month of batches, for example. In addition, HPLC results may be one of the most accurate indications of compositional data available in biofuel production plants 10. Moreover, HPLC results are obtained relatively quickly, for example, in approximately 30 minutes, such that the method 80 enables near real-time determination of performance characteristics, which may enable the process management and control module 58 to make adjustments to a batch before it is complete. Second, because the method 80 enables performance characteristics of individual batches to be determined, operators can more easily evaluate effectiveness of various trials, as described below, rather than relying on monthly data. Finally, the fermenter yield is independent of the particular biomass feedstock 12 because it is defined in terms of a standard of a bushel of corn. Thus, management may be able to compare the performance of several biofuel production plants 10, regardless of biomass feedstock 12, through the remote management and control interface 66.

Figure 3:
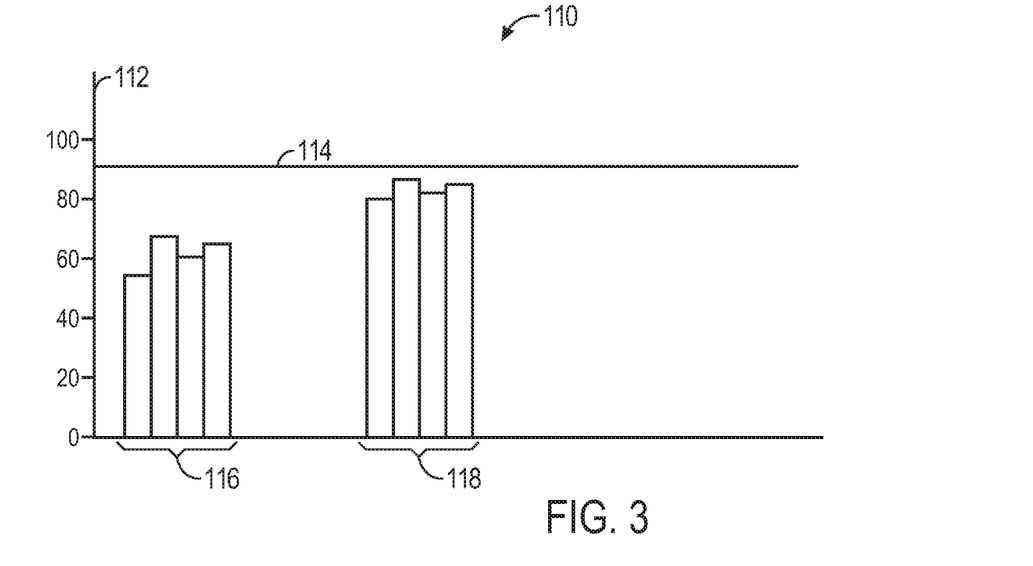
FIG. 3 is a graphical representation of a comparison of two groups of fermenter efficiencies determined using an exemplary method for predicting performance characteristics.

Utilizing the method 80 to determine fermenter performance characteristics described above, FIG. 3 shows a graph 110 of two groups of fermenter efficiency results used to make historical comparisons 54. Other performance characteristics, such as fermenter yields, may be graphed as well. In addition, the information may be presented in formats other than columns, such as, for example, bars, lines, and scatter plots. The ordinate 112 (y-axis) represents the fermenter efficiency from zero to one hundred percent. A maximum theoretical fermenter efficiency 114 is represented by a horizontal line between 80 and 100 percent. A first group 116 may represent fermenter efficiency results for batches from a period in the past, or in other words, historical data. A second group 118 may represent fermenter efficiency results for more recent batches. In FIG. 3, the fermenter efficiencies of the second group 118 are greater than that of the first group 116 and are closer to the maximum efficiency 114. Thus, it appears that operation of the biofuel production plant 10 has improved compared to the historical data. Based on the historical comparisons 54, operators may be able to control the fermentation reactions to produce future batches with improved performance characteristics by controlling operating parameters, such as temperature, enzyme dosing, or combinations thereof.

Alternatively, the graph 110 of FIG. 3 may represent the use of fermenter efficiency results from trial evaluations 56. The first group 116 in FIG. 3 may represent fermenter efficiency results for batches using a standard yeast. The second group 118 may represent the fermenter efficiency results for trials using an improved yeast. Again, the results for the second group 118 are better and closer to the maximum efficiency 114 than those of the first group 116. Thus, it appears that the improved yeast has enabled the biofuel production plant 10 to have higher fermenter efficiencies compared to the use of the standard yeast. Other useful comparisons for maintaining or improving plant performance may be made by plotting fermenter efficiencies in graphs such as graph 110. Thus, operators may be able to select process control strategies, operating conditions and/or parameters, recipes, fermenter charge compositions, enzymes, additives, yeasts, and/or other variables that increase ethanol production and improve plant operations. For example, operating parameters may include temperature, enzyme dosing, or combinations thereof.

Figure 4:
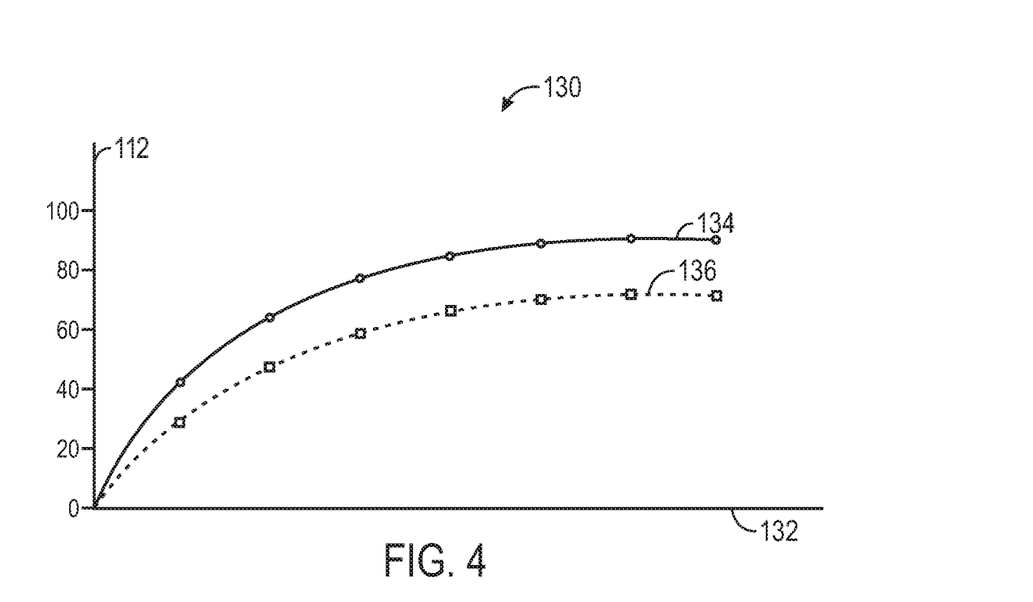
FIG. 4 is a graphical representation of a comparison of two trajectories of fermenter efficiencies determined using an exemplary method for predicting performance characteristics.

In addition to end-of-batch performance, the method 80 may be used to obtain performance characteristics during a fermenter batch. For example, FIG. 4 shows a graph 130 of fermenter efficiency results during two different batches. Other performance characteristics, such as fermenter yields, may be graphed as well. In addition, the information may be presented in formats other than lines, such as, for example, bars, columns, and scatter plots. The points represent the calculated fermenter efficiencies based on results of the fermenter circulation samples 34. In other words, HPLC sample results may be obtained at regular intervals during fermenter batches, which may enable fermenter efficiencies to be calculated throughout the progression of the batch. For example, samples may be obtained approximately 5, 6, 7, 8, 9, or even 10 or more times during a batch, which may last approximately 3 days, for example. However, the actual frequency of sample collection may be based on the needs of a particular application. Returning to FIG. 4, the abscissa 132 (x-axis) represents time and the ordinate 112 represents fermenter efficiency. A first curve 134 shows the fermenter efficiency beginning at zero when the batch begins and gradually increasing until reaching a value between 80 and 100 percent. A second curve 136 shows the same general trend, but increases to a value between 60 and 80 percent. Thus, it appears that the batch represented by the first curve 134 is superior to the batch represented by the second curve 136. Such a batch-by-batch comparison may enable operators or engineers to investigate the causes of dissimilar performance and attempt to replicate the results of superior batches, such as the batch represented by the first curve 134, in the future. Thus, based on such a comparison during fermentation of a batch, operators may be able to adjust operating conditions, timing of recipe steps, duration of the batch, dosing strategy and/or other variables to increase fermenter efficiency, and thus, ethanol production, during the fermentation of the batch.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for controlling operation of a fermenter configured to produce a fermenter batch in a biofuel production plant, comprising:
   determining, using a process controller in the biofuel production plant, a cell mass of a sample of the fermenter batch;
   determining, using the process controller, a glucose equivalent total (GET) of the sample based at least on the cell mass of the sample;
   determining, using the process controller, a starch to glucose conversion factor (SGCF) based at least on the GET of the sample;
   determining, using the process controller, a total amount of glucose in the fermenter batch based at least on the SGCF;
   determining, using the process controller, a volume of ethanol in the fermenter batch based at least on the total amount of glucose and the GET of the sample;
   predicting, using the process controller, a fermenter yield based at least on the volume of ethanol, a fermenter efficiency based on the fermenter yield or the volume of ethanol, or both; and
   controlling, using the process controller, operation of equipment in the biofuel production plant based at least in part upon prediction of the fermenter yield and/or the fermenter efficiency to improve the fermenter yield and/or the fermenter efficiency.

2. The method of claim 1, wherein controlling operation of the equipment comprises comparing the prediction of the fermenter yield and/or the fermenter efficiency against historical data and controlling operation of the equipment based at least in part upon the comparison.

3. The method of claim 2, wherein controlling operation of the equipment comprises controlling operation of the equipment to adjust at least one of temperature, addition of enzymes, or combinations thereof based upon the comparison.

4. The method of claim 3, wherein:
   comparing the prediction of the fermenter yield and/or the fermenter efficiency against the historical data comprises comparing the prediction of the fermenter yield and/or the fermenter efficiency against the historical data during fermentation of the fermenter batch; and
   controlling operation of the equipment comprises controlling operation of the equipment during the fermentation of the fermenter batch.

5. The method of claim 1, wherein the equipment comprises a valve, a motor, a pump, or any combination thereof.

6. The method of claim 1, comprising receiving, using the process controller, results from analysis of the sample, wherein:
   the results comprise concentrations of lactic acid, acetic acid, succinic acid, glycerol, ethanol, glucose, dextrose, other fermented sugars, or combinations thereof in the sample; and
   the sample is drawn from a sample point in the biofuel production plant.

7. The method of claim 1, wherein the fermenter batch comprises backset, wherein characteristics of the backset comprise a weight percent of water, a density of the backset, or combinations thereof.

8. The method of claim 1, wherein characteristics of the fermenter batch comprise a weight percent of water, a weight percent of starch, a weight percent of glucose, or combinations thereof.

9. The method of claim 1, comprising generating, using the process controller, an output comprising a report based at least in part on the prediction of the fermenter yield and/or the fermenter efficiency.

10. The method of claim 9, comprising communicating, using the process controller, the output to an enterprise analyzer, wherein the enterprise analyzer is configured to receive outputs associated with at least two disparate fermenter batches, compare the outputs, and determine performance outputs associated with such comparisons.

11. A method for controlling operation of a fermenter configured to produce a fermenter batch in a biofuel production plant, comprising:
   determining, using a process controller in the biofuel production plant, a cell mass of a sample of the fermenter batch based at least in part on ethanol concentration in the sample;
   determining, using the process controller, a glucose equivalent total (GET) of the sample based at least on the cell mass of the sample and concentration of dextrose, succinic acid, lactic acid, glycerol, and acetic acid in the sample;
   determining, using the process controller, a starch to glucose conversion factor (SGCF) based at least on the GET of the sample, mass of glucose input to the fermenter, mass of starch input to the fermenter, mass of fresh water input to the fermenter, and mass of backset input to the fermenter;
   determining, using the process controller, a total amount of glucose in the fermenter batch based at least on the SGCF, the mass of starch, and the mass of the glucose;
   determining, using the process controller, a volume of ethanol in the fermenter batch based at least on the total amount of glucose, the ethanol concentration, and the GET of the sample;
   predicting, using the process controller, a fermenter yield based at least on the volume of ethanol, a fermenter efficiency based on the fermenter yield or the volume of ethanol, or both; and
   controlling, using the process controller, operation of equipment in the biofuel production plant based at least in part upon prediction of the fermenter yield and/or the fermenter efficiency to improve the fermenter yield and/or the fermenter efficiency.

12. The method of claim 11, wherein controlling the equipment comprises comparing the prediction of the fermenter yield and/or the fermenter efficiency against historical data and controlling operation of the equipment based at least in part upon the comparison.

13. The method of claim 12, wherein controlling operation of the equipment comprises controlling at least one of temperature, addition of enzymes, or combinations thereof based upon the comparison.

14. The method of claim 13, wherein:
   comparing the prediction of the fermenter yield and/or the fermenter efficiency against the historical data comprises comparing the prediction of the fermenter yield and/or the fermenter efficiency against the historical data during fermentation of the fermenter batch; and
   controlling operation of equipment comprises controlling operation of the equipment during the fermentation of the fermenter batch.

15. The method of claim 11, wherein the equipment comprises a valve, a motor, a pump, or any combination thereof.

16. The method of claim 11, comprising receiving, using the process controller, results from analysis of the sample, wherein the sample is drawn from a sample point in the biofuel production plant comprising a biomass sample point, a fermenter circulation sample point, a recirculation loop sample point, a fermenter drop sample point, a biofuel sample point, or a backset sample point.

17. A method for controlling operation of a fermenter configured to produce a fermenter batch in a biofuel production plant, comprising:
   receiving, using a process controller in the biofuel production plant, results from analysis of a sample drawn from a sample point in the biofuel production plant;
   determining, using the process controller, a cell mass of the sample based at least in part on the results;
   determining, using the process controller, a glucose equivalent total (GET) of the sample based at least on the cell mass and the results;
   determining, using the process controller, a starch to glucose conversion factor (SGCF) based at least on the GET of the sample, mass of glucose input to the fermenter, mass of starch input to the fermenter, mass of fresh water input to the fermenter, and mass of backset input to the fermenter;
   determining, using the process controller, a total amount of glucose in the fermenter batch based at least on the SGCF, the mass of the starch, and the mass of the glucose;
   determining, using the process controller, a volume of ethanol in the fermenter batch based at least on the total amount of glucose, the results, and the GET of the sample;
   predicting, using the process controller, a fermenter yield based at least on the volume of ethanol, a fermenter efficiency based on the fermenter yield or the volume of ethanol, or both; and
   controlling, using the process controller, operation of equipment in the biofuel production plant based at least in part upon prediction of the fermenter yield and/or the fermenter efficiency to improve the yield and/or the efficiency of the fermenter.

18. The method of claim 17, wherein controlling operation of the equipment comprises comparing the prediction of the fermenter yield and/or the fermenter efficiency against historical data and controlling operation of the equipment based at least in part upon the comparison.

19. The method of claim 18, wherein controlling operation of the equipment comprises controlling at least one of temperature, addition of enzymes, or combinations thereof based upon the comparison.

20. The method of claim 19, wherein:
   comparing the prediction of the fermenter yield and/or the fermenter efficiency against the historical data comprises comparing the prediction of the fermenter yield and/or the fermenter efficiency against the historical data during fermentation of the fermenter batch; and
   controlling operation of equipment comprises controlling operation of the equipment during the fermentation of the fermenter batch.

21. The method of claim 17, wherein the equipment comprises a valve, a motor, a pump, or any combination thereof.

22. The method of claim 17, wherein the sample comprises a biomass sample, a fermenter circulation sample, a recirculation loop sample, a fermenter drop sample, a biofuel sample, or a backset sample.

* * * * *